United States Patent [19]

Jalalian et al.

[11] Patent Number: 5,399,672
[45] Date of Patent: Mar. 21, 1995

[54] PROCESS FOR PREPARING IMMUNOCONJUGATES

[75] Inventors: Mohammad Jalalian, Reinheim; Arnulf Heubner, Mainz; Bernd Reckmann, Seeheim, all of Germany

[73] Assignee: Merck Patent Gesellschaft mit beschrankter Haftung, Darmstadt, Germany

[21] Appl. No.: 155,897

[22] Filed: Nov. 23, 1993

[30] Foreign Application Priority Data

Nov. 24, 1992 [DE] Germany .................. 42 39 429.5

[51] Int. Cl.⁶ .................. C07K 3/00; G01N 33/531
[52] U.S. Cl. .................. 530/403; 530/345;
530/406; 530/404; 530/405; 530/363; 530/807;
530/391.1; 530/391.3; 530/391.5; 530/391.7;
530/391.9; 435/188; 435/964; 436/543;
436/544; 436/545; 436/546; 436/815; 436/822;
436/823
[58] Field of Search .............. 530/363, 403, 404, 405,
530/406, 408, 409, 410, 411, 807, 391.1, 391.3,
391.5, 391.7, 391.9, 345; 435/188, 964; 436/543,
544, 545, 546, 815, 822, 823

[56] References Cited

U.S. PATENT DOCUMENTS

| | | | |
|---|---|---|---|
| 3,875,011 | 4/1975 | Rubenstein et al. | 195/99 |
| 4,065,354 | 12/1977 | Ullman et al. | 195/63 |
| 4,069,105 | 1/1978 | Singh | 195/63 |
| 4,235,969 | 11/1980 | Singh et al. | 435/188 |
| 4,262,089 | 4/1981 | Singh et al. | 435/7 |
| 4,275,160 | 6/1981 | Singh et al. | 435/188 |
| 4,307,245 | 12/1981 | Hu et al. | 562/442 |
| 4,446,065 | 5/1984 | Lin et al. | 530/389.8 |
| 4,578,350 | 3/1986 | Armenta et al. | 435/7 |
| 4,727,022 | 2/1988 | Skold et al. | 437/7 |

Primary Examiner—Michael G. Wityshyn
Assistant Examiner—C. Sayala
Attorney, Agent, or Firm—Millen, White, Zelano & Branigan

[57] ABSTRACT

The invention relates to a novel process for preparing immunoconjugates consisting of haptens which are sparingly soluble or insoluble in aqueous solution and proteins/polypeptides using special solvents, in particular diethylene glycol monoalkyl ethers.

21 Claims, No Drawings

PROCESS FOR PREPARING IMMUNOCONJUGATES

SUMMARY OF THE INVENTION

The invention relates to a novel process for preparing immunoconjugates comprising a hapten which is sparingly soluble or insoluble in aqueous solution and protein/polypeptide, with the optional inclusion of spacers or crosslinkers.

Immunoconjugates play an increasingly important role in immunodiagnostics and immunotherapy. Correspondingly, importance is also attached to viable and economic processes for preparing such immunoconjugates.

According to the methods described in the standard literature, an immunoconjugate is prepared in an aqueous, as a result buffered, medium by coupling a correspondingly modified hapten to a protein or polypeptide either directly or indirectly via suitable crosslinkers or spacers, and is subsequently purified by standard methods.

The success of the coupling of this nature is heavily dependent on the solubility in the aqueous (buffer) medium of the hapten employed. However, many haptens, in particular drugs or drug derivatives, are either insoluble or only very sparingly soluble in water or aqueous buffer, although they may on the other hand be soluble in most common organic solvents. However, most of the proteins/polypeptides which are employed for these purposes and serve as coupling components become denatured in organic solvents, for the most part in an irreversible manner, so that no biologically active conjugates can be obtained. The salt form, into which many haptens can in principle be converted, is as a rule unsuitable for use in immunogen synthesis.

An object therefore was to develop a process for preparing conjugates, e.g., with immunogen activity, which process also permits the employment of haptens, in particular drug derivatives, which are either insoluble or only sparingly soluble in aqueous medium.

It has now been found that certain organic solvents are able to dissolve, in adequate quantity, the hapten components which are sparingly soluble in aqueous medium, without the protein component being denatured in the process.

The invention thus relates to a process for preparing immunoconjugates which comprise a hapten (A) which is sparingly soluble in aqueous solution and of a protein or polypeptide (B), with the optional inclusion of a crosslinker or spacer, characterized in that the coupling reaction between (A) and (B), and optionally the crosslinker or spacer, is essentially carried out in one of, or in a mixture of, the solvents listed below:
- diethylene glycol monoalkyl ether, in which the alkyl radical can have 1 to 6 C atoms;
- diethylene glycol dialkyl ether, in which the alkyl radical can have 1 to 6 C atoms;
- 1,3-dimethyl-2-imidazolidinone or 1,3-dimethylimidazolidin-2-one (DMI);
- gamma-butyrolactone;
- glycerol formal or
- 2,2-dimethyl-4-hydroxymethyl-1,3-dioxolane It was also found that those haptens are in particular suitable which possess a chemically reactive radical; in particular, appropriately modified amiodarone derivatives are suitable. Haptens, carriers and crosslinkers or spacers, are generally known in the art, e.g., as described in Mazid et al., *Bioconjugate Chem.* 2, 32 (1991); Lemieux et al., *J. Am. Chem. Soc.*, 97, 4076 (1975); Lemieux et al., *Can. J. Biochem.*, 55, 507 (1977); *Advances in Carbohydrate Chemistry*, 37, 225 (1980).

The invention thus relates to a corresponding process which is characterized in that the hapten contains a group of the formula

in which
X is O, S or NR',
Y is NHR', COR, SH, OH, CN or halogen,
R is $NH_2$, halogen or OR',
R' is H or alkyl having 1 to 4 C atoms, and
n is an integer from 1 to 10.

The invention relates, in particular, to a corresponding process in which the hapten is an amiodarone derivative of the formula I,

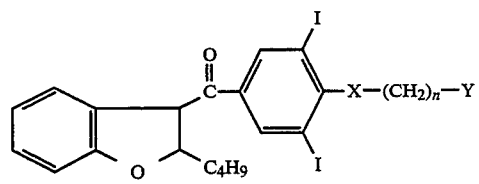

in which X, Y and n have the given meanings.

According to the invention, the expression "sparingly soluble in aqueous medium" denotes that the solubility of the corresponding derivative in water or aqueous buffer is, for example, less than 200 mmol/l at a pH of about 6.5 to 7.5.

The solvents according to the invention can be employed either individually or mixed together. When the different solvents are mixed together, the amount of each is determined routinely, e.g., in amounts which dissolve the hapten, protein or polypeptide, and optionally the spacer or crosslinker, without deleteriously affecting them. Many hapten derivatives, in particular the compounds of the formula I, can be dissolved surprisingly well in these solvents. What is more, the said solvents possess an important advantage that they are able satisfactorily to dissolve very many of the proteins/polypeptides which are commonly used for coupling reactions, without thereby causing any significant degree of noticeable denaturation. In addition, the solvents according to the invention have the advantage that they are miscible with water, so that the common crosslinkers or spacers, which are to be inserted, if desired, between the hapten and protein component, can also be employed in the coupling reaction. The solvent diethylene glycol monoethyl ether (Carbitol ®) is particularly preferred.

In preparation for the desired coupling reaction, the hapten derivatives (which are either sparingly soluble or insoluble in aqueous medium) are dissolved in the corresponding solvent, with concentrations preferably being adjusted to 0.01 to 3 mol/l. In the last analysis, the concentration which is achievable depends on the chemical nature of the respective hapten. The concentration of the preferred amiodarone derivatives of the formula I in the respective soluble is preferably 0.01 to 0.5 mol/l.

Compounds (which are either sparingly soluble or insoluble in aqueous medium), preferably drug derivatives or peptides, containing a chemically reactive functional group which is capable of reacting with an amino, SH, OH or carboxyl radical of the protein/polypeptide component, are suitable as the hapten component. Those derivatives, in particular, are suitable which contain the radical

in which
X is O, S or NR',
Y is NHR', COR, SH, OH, CN or halogen,
R is $NH_2$, halogen or OR',
R' is H or alkyl having 1 to 4 C atoms, and
n is an integer from 1 to 10.

Alkyl is thus methyl, ethyl, propyl, isopropyl, n-butyl, sec-butyl or tert-butyl, preferably methyl or ethyl. X is preferably O or NR' and Y is preferably COR or NHR'. Halogen is preferably Cl or Br. n is preferably 2 to 6.

Radicals of this nature can as a rule readily be introduced by standard methods into the corresponding hapten, e.g., a drug derivative. For example, hapten components containing phenolic OH groups, SH groups or NHR groups can be reacted with halocarboxylic acid derivatives to give the corresponding reactive components which are capable of conjugate formation, for example the amiodarone derivatives of the formula I.

However, reactions with suitable activated double bonds or amino groups, for example, can also be carried out by methods which are known per se.

The proteins which are provided for the coupling reaction are preferably dissolved in the same solvent as the hapten component, with the concentration to be set depending once again on the chemical nature of the protein. Preferably, adjustment is made to give concentrations of 0.1–300 μmol/l, in particular 5–150 μmol/l.

All proteins or polypeptides which are commonly used for these purposes, for example, bovine serum albumin (BSA), keyhole limpet haemocyanin (KLH), IgG, ovalbumin, lactalbumin or thyroglobulin, are suitable as the protein component.

If desired, spacer molecules or crosslinkers, which are commonly known for these purposes, can be inserted by standard methods between the hapten component and protein/polypeptide component. Examples of such compounds are N-hydroxysuccinimide (NHS), N-(3-dimethylaminopropyl)-N'-ethylcarbodiimide hydrochloride (EDC), N,N'-dicyclohexylcarbodiimide (DCC), 1-cyclohexyl-3-(2-morpholinoethyl)carbodiimide (CMC), or compounds of the type $Z-(CH_2)_n-Y$, in which Z is XH or halogen, and X and Y have the given meanings. Preferably, these compounds are likewise dissolved in the same solvent as the other two components, or else initially dissolved in a little water and then mixed with the respective solvent which already contains the other components in dissolved form.

The solutions, according to the invention, of hapten component, protein component and, optionally, crosslinker/spacer component can also, according to the invention, contain water and/or other common, organic solvents, such as, for example, DMSO, DMF, methanol or ethanol, which as a rule, without the solvents according to the invention, bring about an irreversible denaturation of the protein.

The amount of these other solvents in a solution according to the present invention must be less than the amount which would cause irreversible denaturation or be otherwise deleterious to the protein/polypeptide component and/or hapten component. This amount is, e.g., generally not more than 50% (v/v) of the solution.

The proportion of water must not be so great that the hapten or protein component in question begins to precipitate out. According to the invention, the proportion of water can be, e.g., 0–50%, preferably 10–30%.

The conjugation of hapten to a protein or polypeptide, and optionally a crosslinker or spacer, in the presence of solvents according to the invention otherwise proceeds under conditions which are known from the standard literature (e.g., Colbert et al., Ann. Clinical Biochem. 23, 37 (1986). Adjustment of the reaction conditions for a specific solvent or mixture thereof can be routinely accomplished.

In the process according to the invention, drug derivatives, such as, for example, the compounds of the formula I, are preferably employed as the hapten component. A compound of this type is amiodarone (2-butyl-3-[3,5-diiodo-4-(β-diethylaminoethoxy)-benzoyl]benzofuran). Amiodarone is used therapeutically as an antiarrhythmic agent. Further examples of suitable drugs are phencyclidine, tetrahydrocannabinol, quinine or quinidine. The immunoconjugates prepared from these substances by the process according to the invention can be used according to known methods for immunizing mice, for example. The amounts of immunoconjugate used to elicit an immune response can be determined routinely. The antibodies obtained in this way can then, for example, be used for the immunological detection of drugs, drug derivatives or drug metabolites in human body fluids. The conjugates prepared according to the present invention can also be used as standards or competitors in assays, as carriers for drugs, and in other ways for which conjugates are typically used.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all publications, cited above, and of corresponding application P 42 39 429.5, filed Nov. 24, 1992, are hereby incorporated by reference.

EXAMPLES

Example 1

32.8 g (60 mmol) of 2-butyl-3-[3,5-diiodo-4-hydroxybenzoyl]benzofuran and 13.8 g (100 mmol) of anhydrous potassium carbonate are initially introduced into 200 ml of acetonitrile. 17.6 g (90 mmol) of ethyl 4-bromobutyrate are added dropwise at room temperature within the space of 30 minutes and the suspension is subsequently heated under reflux for 14 h. Once the reaction solution has been cooled down to room temperature, 200 ml of distilled water are added and the mixture is extracted 3 times with 100 ml of methyl tert-butyl ether. The combined organic extracts are dried and concentrated to dryness. The residue, which consists of 2-butyl-3-[3,5-diiodo-4-(3-ethoxycarbonylpropyloxy)benzoyl]benzofuran, is introduced into 100 ml of isopropanol and a solution of 39.6 g (600 mmol) of 85% potassium hydroxide in 400 ml of distilled water is added. The suspension is heated at about 60° C. until a clear solution is formed. Once the solution has been cooled down to room temperature, 100 ml of 1N hydrochloric acid are added, and the mixture is adjusted to pH 3 with 32% hydrochloric acid while cooling, and then extracted 3 times with 200 ml of MTB ether on each occasion. The combined organic, dried, rotary-evaporated extracts are taken up in 50 ml of dichloromethane and left at 0° C. for several hours. The pale brown crystals which have precipitated out are stirred up with a further 50 ml of dichloromethane. After filtering with suction, washing and drying, 5.7 g (20%) of almost colourless crystals of 2-butyl-3-[3,5-diiodo-4-(3-carboxypropyloxy)-benzoyl]benzofuran are obtained which can, if desired, be further purified on a silica gel column (MTB ether/methanol=9:1).

Example 2

230 mg (0.36 mmol) of the amiodarone derivative prepared according to Example 1 are dissolved in 1.5 ml of Carbitol ®. 50 mg (0.72 μmol) of KLH are dissolved in 25 ml of Carbitol ® as well. The two solutions are mixed together and stirred at room temperature for 3 hours. After the reaction is complete, the mixture is dialysed against demineralized water at 4° C. After the dialysis, the solution, which contains the conjugate consisting of amiodarone derivative and KLH, Es used for the immunization.

Example 3

500 μl of demineralized water, in which 57 mg (0.3 mmol) of EDC and 38 mg (0.33 mmol) of NHS have been dissolved, are added to the solution of the amiodarone derivative according to Example 2. This solution is then added to a solution of 50 mg of. BSA in 25 ml of Carbitol ®. The subsequent procedure is as given in Example 2. An immunoconjugate consisting of the amiodarone derivative according to Example 1, the said crosslinkers and BSA is obtained.

Example 4

A derivative consisting of tetrahydrocannabinol and Br—(CH₂)₂—COOH and prepared according to Example 1 is dissolved (250 mg) in 2 ml of diglyme, and a protein solution consisting of 50 mg of KLH in 30 ml of diglyme is added. The subsequent procedure is as given in Example 2. A tetrahydrocannabinol derivative/KLH conjugate is obtained.

Example 5

The amiodarone derivative (230 mg) prepared according to Example 1 is dissolved in 3 ml of Carbitol ®. A solution of 8-ethoxycarbonyloctanol (spacer) in 500 μl of methanol (1:4) is added to this solution. This solution is then mixed with a solution of 50 mg of KLH in 25 ml of Carbitol ® and caused to react as previously described. A corresponding amiodarone derivative/spacer/KLH conjugate is obtained.

Example 6

A quinine derivative which is capable of coupling is prepared according to standard methods. An immunoconjugate containing BSA as the protein component is prepared according to Example 2, a mixture consisting of Carbitol ®/DMI/ethanol (40/40/20) being used as the solvent.

Example 7

A corresponding immunoconjugate is prepared from the amiodarone derivative according to Example 1 together with BSA and EDC (crosslinker), a mixture consisting of Carbitol ®/glycerol formal/H₂O (50/15/35) being used as the solvent.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing an immunoconjugate comprising a hapten (A) which is sparingly soluble in aqueous solution and a protein or polypeptide (B), comprising coupling (A) and (B) in a solvent, with the optional inclusion of a crosslinker or spacer, wherein the solvent is:

a diethylene glycol monoalkyl ether, wherein the alkyl group is $C_1$-$C_6$;

a diethylene glycol dialkyl ether, wherein the alkyl group is $C_1$-$C_6$;

1,3-dimethyl-2-imidazolidinone;

gamma-butyrolactone;

glycerol formal;

2,2-dimethyl-4-hydroxymethyl-1,3-dioxolane; or a mixture thereof, and wherein the content of water in said solvent is from 0% to about 30% (v/V).

2. A process according to claim 1, wherein the solvent is diethylene glycol monoethyl ether.

3. A process according to claim 1, wherein the hapten is a drug.

4. A process according to claim 1, wherein the hapten is an amiodarone compound of the formula

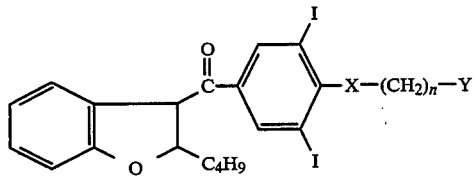

wherein:

X is O, S, or NR';

Y is NHR', COR, SH, OH, CN or halogen;

R is $NH_2$, halogen, or OR';

R' is H or alkyl having 1-4 C atoms; and n is an integer from 1-10.

5. The process according to claim 1, wherein the content of water in said solvent is 0%.

6. The process according to claim 1, wherein the content of water in said solvent is from about 10% to about 30%.

7. The process of claim 1, wherein the solubility of the hapten in water is less than about 200 mmol/l at a pH of about 6.5 to about 7.5.

8. A process according to claim 1, wherein the hapten comprises a group of the formula —X—$(CH_2)_n$—Y, wherein:

X is O, S, or NR';
Y is NHR', COR, SH, OH, CN, or halogen;
R is NH$_2$, halogen, or OR';
R' is H or alkyl having 1–4 C atoms; and
n is an integer from 1–10.

9. A process according to claim 8, wherein X is O or NR'.

10. A process according to claim 8, where Y is COR or NHR'.

11. A process according to claim 8, wherein R' is methyl or ethyl.

12. A process according to claim 8, wherein the halogen is Cl or Br.

13. A process according to claim 8, wherein n is 2 to 6.

14. In a process of preparing a conjugate comprising a hapten and a protein or polypeptide, the improvement comprising coupling said hapten to the protein or polypeptide in a solvent, wherein the solvent is:
a diethylene glycol monoalkyl ether, wherein the alkyl group is C$_1$–C$_6$;
a diethylene glycol dialkyl ether, wherein the alkyl group is C$_1$–C$_6$;
1,3-dimethyl-2-imidazolidinone;
gamma-butyrolactone;
glycerol formal;
2,2-dimethyl-4-hydroxymethyl-1,3-dioxolane; or a mixture thereof,
and wherein the content of water in said solvent is from 0% to about 30% (v/v).

15. The process according to claim 14, wherein the solvent is diethylene glycol monoethyl ether.

16. The process according to claim 15, wherein the hapten comprises a group of the formula —X—(CH$_2$)$_n$—Y, wherein:
X is O, S, or NR';
Y is NHR', COR, SH, OH, CN or halogen;
R is NH$_2$, halogen, or OR';
R' is H or alkyl having 1–4 C atoms; and
n is an integer from 1–10.

17. The process according to claim 15, wherein the hapten is a drug.

18. The process according to claim 15, wherein the hapten is an amiodarone compound of the formula

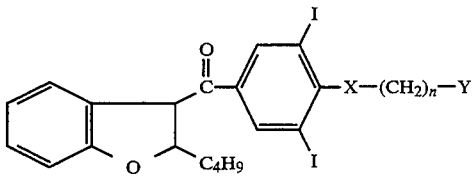

wherein:
X is O, S, or NR';
Y is NHR', COR, SH, OH, CN or halogen;
R is NH$_2$, halogen, or OR';
R' is H or alkyl having 1–4 C atoms; and
n is an integer from 1–10.

19. A mixture containing a conjugate and a solvent, wherein the conjugate comprises:
(A) a hapten which is sparingly soluble in aqueous solution,
(B) a protein or polypeptide, and
(C) optionally, a crosslinker or spacer, and the solvent is:
a diethylene glycol monoalkyl ether, wherein the alkyl group is C$_1$–C$_6$;
a diethylene glycol dialkyl ether, wherein the alkyl group is C$_1$–C$_6$;
1,3-dimethyl-2-imidazolidinone;
gamma-butyrolactone;
glycerol formal;
2,2-dimethyl-4-hydroxymethyl-1,3-dioxolane; or a mixture thereof,
and wherein the content of water in said solvent is from 0% to about 30% (v/v).

20. The mixture according to claim 19, wherein the solvent is diethylene glycol monoethyl ether.

21. A mixture according to claim 19, wherein the solubility of the hapten in water is less than about 200 mmol/l at a pH of about 6.5 to about 7.5.

* * * * *